(12) United States Patent
Aota et al.

(10) Patent No.: US 10,281,439 B2
(45) Date of Patent: May 7, 2019

(54) METHOD OF TRANSMITTING CONTROL DATA FOR SYSTEM CONVERSION AMONG LIQUID CHROMATOGRAPHS

(71) Applicant: HITACHI HIGH-TECHNOLOGIES CORPORATION, Tokyo (JP)

(72) Inventors: Toshimichi Aota, Tokyo (JP); Satoshi Mitsuyama, Tokyo (JP); Masahito Ito, Tokyo (JP); Chihiro Yoshioka, Tokyo (JP); Takaaki Suzuki, Tokyo (JP)

(73) Assignee: Hitachi High-Technologies Corporation, Tokyo (JP)

( * ) Notice: Subject to any disclaimer, the term of this patent is extended or adjusted under 35 U.S.C. 154(b) by 0 days.

(21) Appl. No.: 14/649,336

(22) PCT Filed: Nov. 11, 2013

(86) PCT No.: PCT/JP2013/080463
§ 371 (c)(1),
(2) Date: Jun. 3, 2015

(87) PCT Pub. No.: WO2014/097771
PCT Pub. Date: Jun. 26, 2014

(65) Prior Publication Data
US 2016/0216239 A1 Jul. 28, 2016

(30) Foreign Application Priority Data
Dec. 19, 2012 (JP) .................................. 2012-276357

(51) Int. Cl.
G01N 30/86 (2006.01)
G01N 30/26 (2006.01)
(Continued)

(52) U.S. Cl.
CPC .......... *G01N 30/26* (2013.01); *G01N 30/8651* (2013.01); *G01N 30/16* (2013.01); *G01N 30/34* (2013.01); *G01N 30/8658* (2013.01)

(58) Field of Classification Search
CPC .... G01N 30/8658; G01N 30/26; G01N 30/34; G01N 30/236; B01F 15/0416
(Continued)

(56) References Cited

U.S. PATENT DOCUMENTS

2009/0288473 A1  11/2009  Suzuki et al.
2011/0209766 A1*  9/2011  Witt ....................... G01N 30/34
                                                                        137/1

FOREIGN PATENT DOCUMENTS

JP          7-12799 A     1/1995
JP       2001-281230 A   10/2001
JP       2009-281897 A   12/2009

OTHER PUBLICATIONS

International Search Report of PCT/JP2013/080463.

* cited by examiner

*Primary Examiner* — Lisa M Caputo
*Assistant Examiner* — Irving A Campbell
(74) *Attorney, Agent, or Firm* — Mattingly & Malur, PC

(57) ABSTRACT

In the present invention, differences in liquid feed properties between liquid chromatographic devices are determined, a liquid feed time table that takes these differences into account is acquired by way of system changes, and flow control is performed by a pump. Furthermore, the liquid feed time table after the system changes is divided into a plurality of intervals, and instructions are sent to the pump after approximate calculations are performed. Thus, by efficiently performing system change processes, the same measurement (Continued)

results can be obtained in a plurality of different liquid chromatograph devices, regardless of the differences in liquid feed properties.

20 Claims, 12 Drawing Sheets

(51) Int. Cl.
*G01N 30/34* (2006.01)
*G01N 30/16* (2006.01)

(58) Field of Classification Search
USPC .............................. 73/61.55, 61.57; 702/123
See application file for complete search history.

FIG. 7

| Time (min) | %A | %B | Flow (ml/min) |
|---|---|---|---|
| 0.0 | 90 | 10 | 1 |
| 5.0 | 90 | 10 | 1 |
| 5.1 | 50 | 50 | 1 |
| 10.0 | 50 | 50 | 1 |
| 10.1 | 10 | 90 | 1 |
| 15 | 10 | 90 | 1 |
| 15.1 | 90 | 10 | 1 |
| 20 | 90 | 10 | 1 |

FIG. 13

| INTERVAL No. | START POINT OF INTERVAL | END POINT OF INTERVAL | COEFFICIENT $a_0$ | COEFFICIENT $a_1$ | COEFFICIENT $a_2$ | COEFFICIENT $a_3$ |
|---|---|---|---|---|---|---|
| 1 | $t_1$ | $t_2$ | $a_{1\_0}$ | $a_{1\_1}$ | $a_{1\_2}$ | $a_{1\_3}$ |
| 2 | $t_2$ | $t_3$ | $a_{2\_0}$ | $a_{2\_1}$ | $a_{2\_2}$ | $a_{2\_3}$ |
| ... | | | | | | |
| K | $t_k$ | | $a_{k\_0}$ | $a_{k\_1}$ | $a_{k\_2}$ | $a_{k\_3}$ |
| ... | | | | | | |

METHOD OF TRANSMITTING CONTROL DATA FOR SYSTEM CONVERSION AMONG LIQUID CHROMATOGRAPHS

TECHNICAL FIELD

The present invention relates to a liquid chromatograph and particularly relates to system conversion among a plurality of liquid chromatographs.

BACKGROUND ART

An analytical technique using a liquid chromatograph needs to be highly accurate. A measuring method can be exemplified as contents to be set in the liquid chromatograph when a chromatogram is measured, and examples thereof include a flow rate, a sample injection amount, a temperature setting of a column oven, a sampling interval of a detector, and a response.

PTL 1 discloses a technique for acquiring a correction value using data or the like of a column at the time of conversion of a measuring method of a certain device (conventional liquid chromatograph) to a measuring method of another device (ultrahigh velocity liquid chromatograph) with linear velocity (velocity at which a certain component passes through a column) which is higher than that of the certain device.

CITATION LIST

Patent Literature

PTL 1: JP-A-2009-281897

SUMMARY OF INVENTION

Technical Problem

However, in a case where the same measuring method is used in liquid chromatographs different from each other, the retention time or the degree of separation of the chromatographs may vary due to differences between tube diameters, dead volume of pumps, liquid mixing performance of mixers, dead volume of samplers, sample diffusion capacities other than columns, and detectors.

On the contrary, for example, a user who introduces a new liquid chromatograph for pharmaceutical development or the like wants to obtain the same measurement results as those of a device in the related art without developing a new measuring method even when the new device is used in many cases.

However, the same measurement results cannot be obtained between devices whose specifications are different from each other as described above using the technique disclosed in PTL 1.

For this reason, in the technique in the related art, a known method cannot be used when a device is changed and a different method needs to be developed for each device.

Solution to Problem

According to an aspect in order to solve the above-described problems, there is provided a liquid chromatograph including a liquid chromatograph unit which includes an elution unit sending an eluent to a detecting unit; and a control unit which controls elution performed by the elution unit based on a predetermined time table, in which the control unit stores an elution response of the liquid chromatograph unit to be obtained when a predetermined command value is input to the elution unit and an elution response of another liquid chromatograph to be obtained when the command value is input to another elution unit of another liquid chromatograph and converts the time table based on the elution response and another elution response such that an elution profile at the time when the elution unit is controlled by the liquid chromatograph unit based on the time table approaches another elution profile at a time when another elution unit is controlled by another liquid chromatograph based on the time table, and controls the elution unit based on the converted time table.

In addition, the converted time table is divided into a plurality of regions, approximate calculation is performed for each of the divided regions, and the size of the divided regions is changed based on the results of the approximate calculation.

Advantageous Effects of Invention

According to the above-described aspect, a measuring method related to one device can be used in another device and thus the measuring method can be seamlessly transferred between devices.

In addition, when a fluid is controlled based on a time table after system conversion, it is possible to control an elution unit with high precision and high efficiency in regard to information related to complicated and various time tables.

BRIEF DESCRIPTION OF DRAWINGS

FIG. 7 is a diagram illustrating an example of an elution time table of the present invention.

FIG. 13 is a diagram illustrating a table of results of approximate calculation.

DESCRIPTION OF EMBODIMENTS

Hereinafter, embodiments of the present invention will be described in detail in reference to the accompanying drawings.

Example 1

Figure 1:
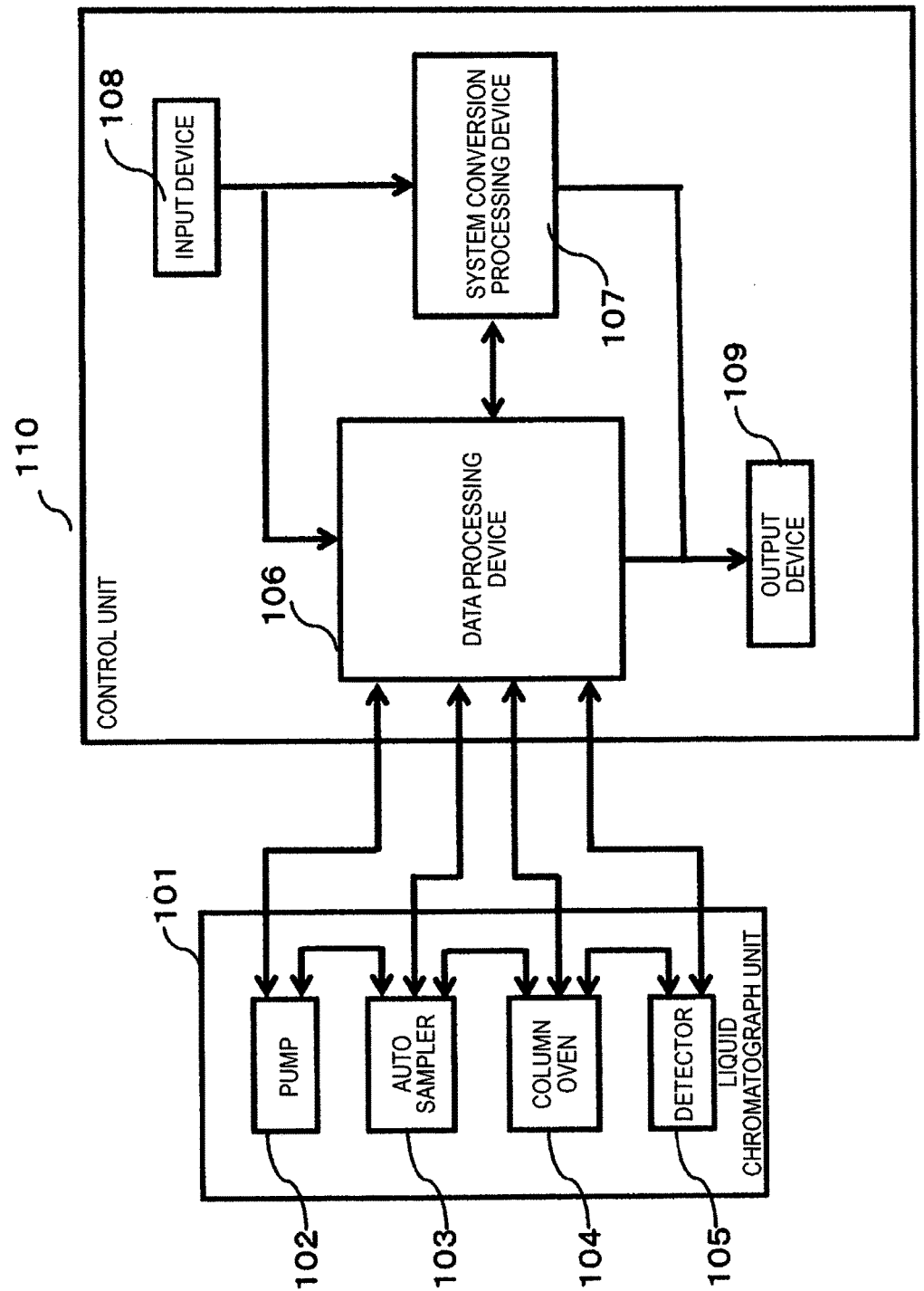
FIG. 1 is a diagram illustrating a system configuration of a liquid chromatograph according to the present invention.

FIG. 1 illustrates a system configuration of a liquid chromatograph in the present invention. The liquid chromatograph illustrated in the figure includes a liquid chromatograph unit 101 in which separation and analysis of a sample are performed and a control unit 110 which is a control device for controlling each device related to the liquid chromatograph unit 101 based on a predetermined measuring method.

The liquid chromatograph unit 101 includes a pump (elution unit) 102 that sends an eluent based on a command from the control unit 110; an auto sampler (sample injection unit) 103 that injects a sample with respect to the eluent from the pump 102 based on a command from the control unit 110; a column oven (separating unit) 104 that holds the temperature of an analysis column 207 (see FIG. 2) based on a command from the control unit 110; and a detector (detecting unit) 105 that detects a component eluted from the analysis column 207 and converts the component into an electrical signal to be output to the control unit 110.

The control unit 110 includes a data processing device 106 that transceives commands and data among respective devices related to the liquid chromatograph unit 101; an input device (for example, a pointing device, a keyboard, and a tablet) 108 to which a command or the like from an operator is input; a system conversion processing device 107 that performs a process (system conversion process) of converting a measuring method input through the input device 108; and an output device 109 on which detection results of a detector 105 and a graphical user interface (GUI) related to various operations of the liquid chromatograph unit 101 and the control unit 110 are shown. Measurement values of each component detected by the detector 105 are taken in the data processing device 106 and analysis results of samples are transmitted to and displayed on the output device 109.

In the measuring method, data columns (hereinafter, also referred to as a "time table" or "elution time table") which are time series of control command values (target values of the elution profile) to the pump 102 and in which a time change of the elution profile of an eluent due to the pump 102 is determined in advance are included. Examples of the control command values include the flow rate and the pressure of an eluent and the mixing ratio of respective eluents in a predetermined flow rate in a case where a plurality of eluents are present. Specific examples of the time table of the pump 102 will be described below. In the present embodiment, system conversion will be described by exemplifying a case where measurement in another liquid chromatograph is reproduced by converting the time table of the pump 102. As described below, the system conversion device 107 performs conversion of the time table (system conversion) based on a difference between elution responses of respective liquid chromatographs such that the "elution profile" shown when the same time table is used in another liquid chromatograph is actually shown in the liquid chromatograph of the present embodiment.

The elution response indicates an actual elution profile of each liquid chromatograph obtained when a predetermined command value (specific examples of the command value will be described below) is input to the pump 102. For example, in a case where the same command value is input to a plurality of liquid chromatographs, the elution profiles vary due to a difference among various specifications (for example, differences between tube diameters, dead volumes of pumps, liquid mixing performance of mixers, dead volumes of samplers, sample diffusion capacities other than columns, and detectors) in the plurality of liquid chromatographs. That is, an elution response becomes an intrinsic value of each liquid chromatograph.

As a method of measuring an actual elution response (elution profile), a method of measuring absorbance of an eluent sent by the pump 102 based on a predetermined command value can be exemplified. The detector 105 installed in the liquid chromatograph unit 101 can be used as means for measuring the absorbance of an eluent.

In addition, it is preferable that command values input to pumps of respective liquid chromatographs when elution profiles are acquired are the same as each other, but the command values may not be perfectly matched if the detection results of the detector 105 are ultimately the same.

Figure 2:
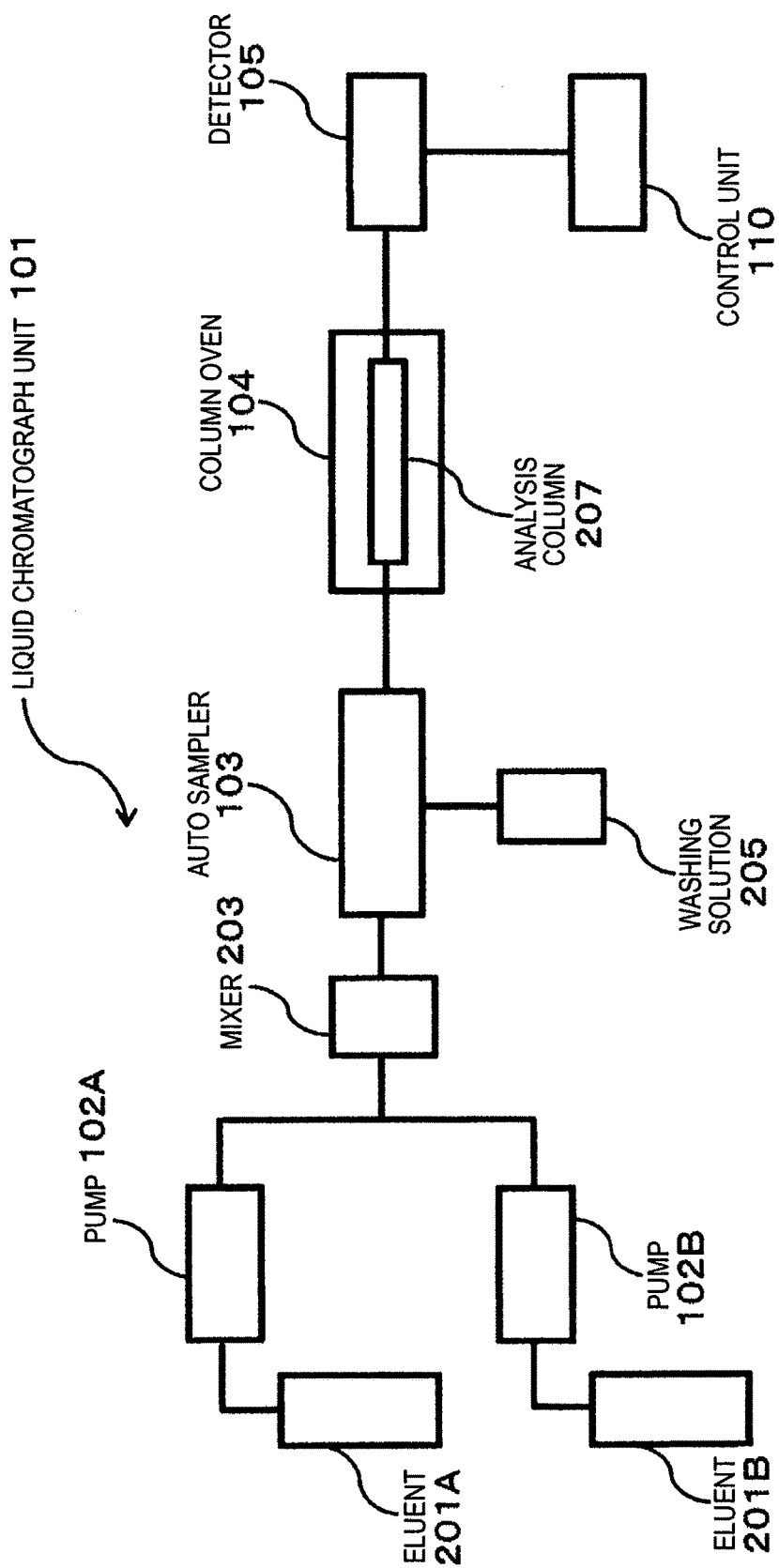
FIG. 2 is a diagram illustrating a system channel of the liquid chromatograph according to the present invention.

FIG. 2 illustrates a system channel of the liquid chromatograph in the present invention. In addition, the same elements in the figure described above are denoted by the same reference numerals and the description thereof is not repeated (the same applies hereinafter). The liquid chromatograph unit 101 illustrated in the figure includes the pumps 102 (a pump 102A sending out an eluent 201A and a pump 102B sending out an eluent 201B, a mixer 203, the auto sampler 103, the column oven 104, and the detector 105.

The pumps 102A and 102B pump the eluents 201A and 201B based on the contents of the time table stored in the data processing device 106. The eluents sent from the pump 102A and 102B are mixed by the mixer 203 and then sent to the column oven 104 through the auto sampler 103. Meanwhile, a sample is injected from the auto sampler 103 and sent to the analysis column 207. The detector 105 detects sample components having passed through the analysis column 207 and the detection results are stored in a storage device of the data processing device 106 of the control unit 110.

Figure 4:
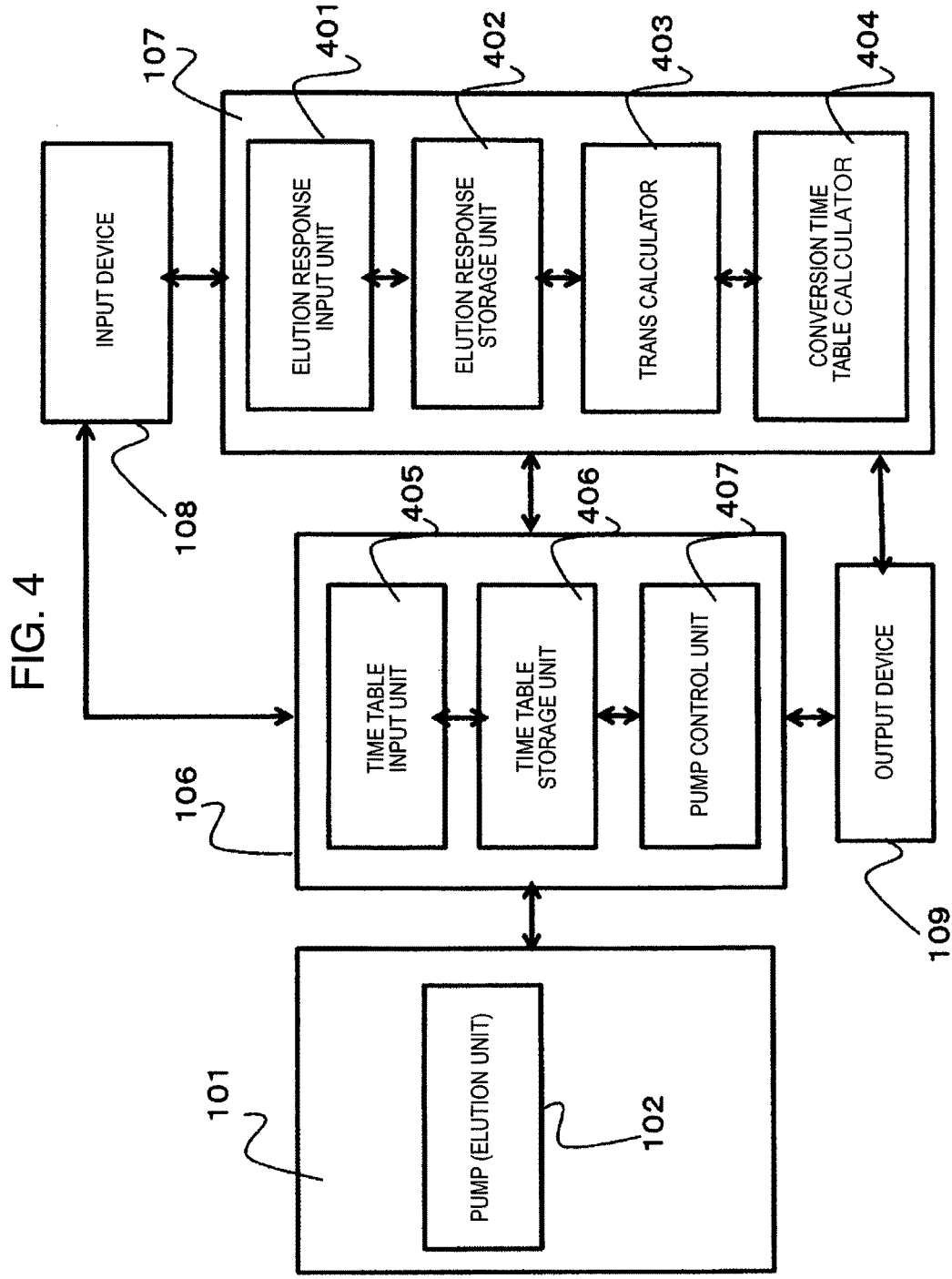
FIG. 4 is a diagram illustrating a part of a system configuration of a data processing device 106 and a system conversion processing device 107 according to a system conversion process of the present invention.

FIG. 4 illustrates a part of the system configuration diagram of the data processing device 106 and the system conversion processing device 107 of the present invention. Further, although not illustrated in the figure, the data processing device 106 and the system conversion processing device 107 respectively include an arithmetic processing device (for example, a CPU) serving as arithmetic means for performing various programs; storage devices (for example, a semiconductor memory such as a ROM, a RAM, or a flash memory, and a magnetic storage device such as a hard disk) serving as storage means for storing the programs and various pieces of data; and an input and output arithmetic processing device for controlling input and output of data, commands, and the like to respective devices 101, 106, 107, 108, and 109.

In FIG. 4, the data processing device 106 includes a time table input unit 405, a time table storage unit 406, and a pump control unit 407.

The time table input unit 405 is a portion to which a time table related to the control of the pumps 102 (pumps 102A and 102B) is input from the outside. Examples of the method of inputting the time table include a method of inputting the time table through a storage medium in which the time table is stored and a method of inputting the time table using communication through another computer and a network in addition to a method of inputting the time table using the input device 108.

The time table storage unit 406 is a portion in which a time table input through the time table input unit 405 and a time table converted by a conversion time table calculator 404 in the system conversion processing device 107 described below are stored.

The pump control unit 407 is a portion that controls the pumps 102 (pumps 102A and 102B) of the liquid chromatograph unit 101 based on the time table stored in the time table storage unit 406. In a case where data to which the conversion time table calculator 404 is converted is selected as a time table used here, the pump control unit 407 controls the pumps 102 (the pump 102A and the pump 102B) based on the time table.

In FIG. 4, the system conversion processing device 107 includes an elution response input unit 401, an elution response storage unit 402, a re-calculator 403, and the conversion time table storage unit 406.

The elution response input unit 401 is a portion to which elution responses of a plurality of liquid chromatographs including the liquid chromatograph unit 101 are input. Examples of the method of inputting elution responses to the input unit 401 include a method of inputting the elution responses through a storage medium in which the elution responses are stored and a method of inputting the elution responses using communication through another computer in which the elution responses are stored and a network in addition to a method of inputting the elution responses using the input device 108.

The elution response storage unit 402 is a portion in which the elution responses of a plurality of liquid chromatographs (including the liquid chromatograph unit 101) input through the elution response input unit 401 are stored.

The trans calculator 403 is a portion that calculates a trans (trans(t)) between elution responses of the liquid chromatograph unit 101 and another liquid chromatograph. The contents of the calculation will be described below.

The conversion time table calculator 404 is a portion that stores a time table which is stored in the time table storage unit 406 and used for sample analysis based on the trans of the elusion response calculated by the trans calculator 403. As a case where a time table is converted by the conversion time table calculator 404, a case where measurement results obtained in a certain device (liquid chromatograph A) using a predetermined time table are reproduced in another device (liquid chromatograph B) can be exemplified. A specific conversion process is as described above with reference to FIG. 3.

Figure 3:
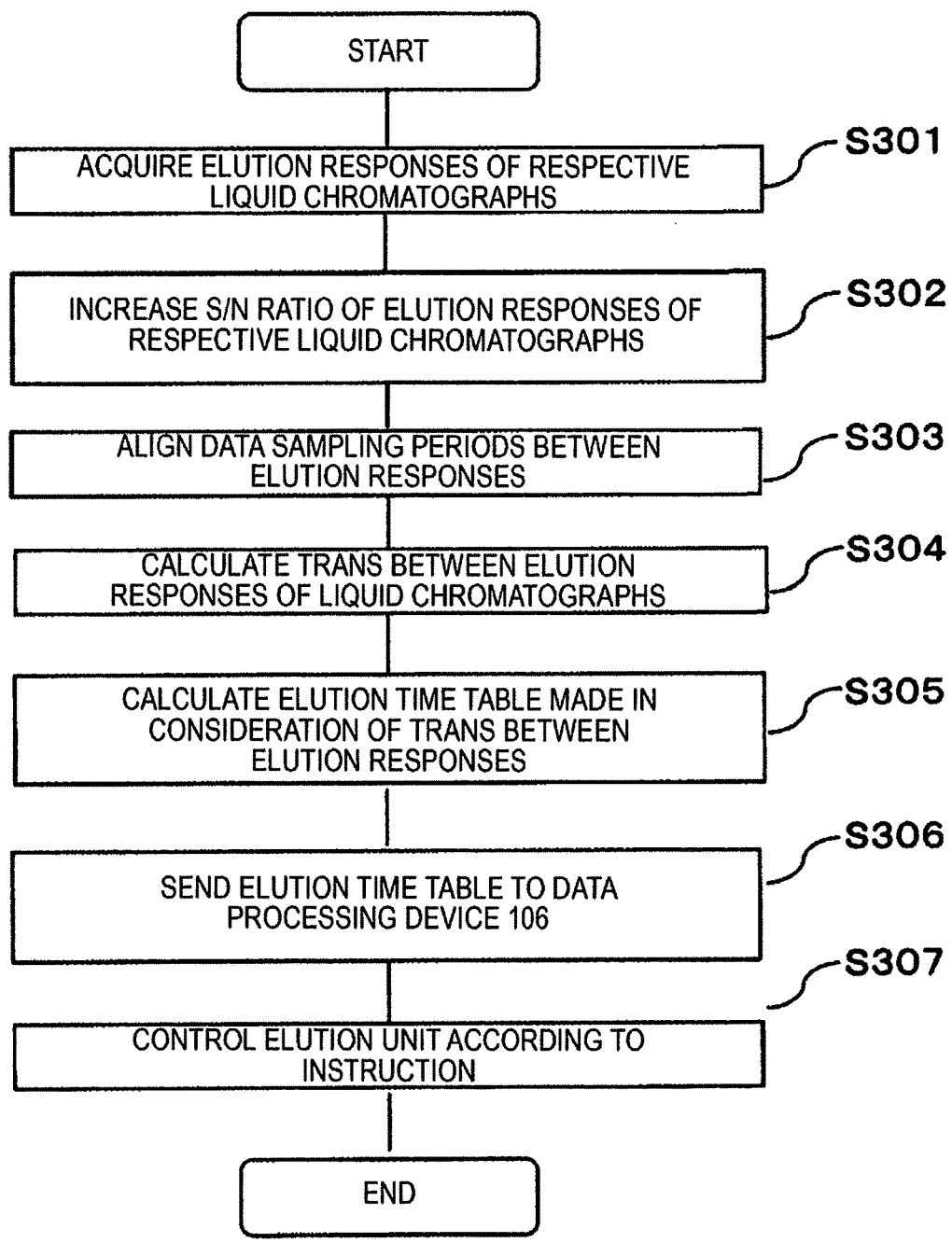
FIG. 3 is a flowchart illustrating a method of processing a system conversion program according to the present invention.

FIG. 3 is a flowchart showing a method of processing a system conversion program in the present invention. A method of controlling the pump 102 using system conversion will be described below with reference to this figure.

Here, under the assumption that the two liquid chromatographs A and B which are different from each other and a common time table related to control of pumps of the respective liquid chromatographs A and B are present, a case of performing system conversion of the liquid chromatograph B such that measurement results obtained when the pump is controlled by the liquid chromatograph B based on the time table approach measurement results obtained when the pump is controlled by the liquid chromatograph A based on the time table will be described. Here, the description will be made under the assumption that the liquid chromatograph B corresponds to a liquid chromatograph illustrated in FIGS. 1 and 2 and the liquid chromatograph A has the same configuration as that illustrated in at least FIG. 2.

In FIG. 3, first, the system conversion processing device 107 acquires elution responses of the liquid chromatograph A and the liquid chromatograph B through the elution response input unit 401 (see FIG. 4) and stores the elution responses in the elution response storage unit 402 (S301). The elution responses of the liquid chromatograph A and the liquid chromatograph B are derived from respective tube systems, the dead volumes of the pumps 102A and 102B, sample diffusion capacities other than columns, and the detectors 105. Here, the elution response of the liquid chromatograph A is set as RA(t) and the elution response of the liquid chromatograph B is set as RB(t).

The elution responses RA(t) and RB(t) are obtained by measuring actual elution profiles of respective liquid chromatographs A and B when the same command value is input to the pumps 102A and 102B of the liquid chromatographs A and B. The elution responses (actual elution responses) of the liquid chromatographs A and B can be acquired by measuring the absorbance of the eluent sent through the pumps 102A and 102B and the mixer 203 using the detectors 105 of respective devices A and B. The elution responses RA(t) and RB(t) acquired in this manner are stored in the elution response storage unit 402 through the input device 108 or the like.

At this time, a process of increasing the S/N ratio of the elution response if necessary (S302) and a process of adjusting data sampling periods to be the same among elution responses (S303) are performed.

The process of increasing the S/N ratio of the elution response obtained through actual measurement can be performed by carrying out a smoothing process according to any one of a moving-average method, a Savitzky-Golay method, a Kawata-Minami method, and a frequency domain method, or a combination of these.

Further, as a method of adjusting the data sampling periods among elution responses, it is preferable to use interpolation such as linear interpolation, spline interpolation, polynomial interpolation, continued fraction interpolation, or a trigonometric function.

In the liquid chromatograph, the measurement results (actual elution profile of an eluent) obtained when the pumps 102A and 102B are controlled based on the elution time table (that is, command values related to a time change of mixing ratios of the eluent 201A and the eluent 201B) as illustrated in FIG. 7 are shown by the following equations (1) and (2) using the elution responses RA(t) and RB(t). Further, the actual elution profile of an eluent can be acquired by measuring the absorbance of the eluent using the detector 105 in the same manner as that of the elution response. Here, the symbol "*" represents a convolution operation.

[MATH. 1]

$$\text{Measurement results of liquid chromatograph } A \text{ when Time Table is input} = \text{Time Table} * RA(t) \quad \text{Equation (1)}$$

[MATH. 2]

$$\text{Measurement results of liquid chromatograph } B \text{ when Time Table is input} = \text{Time Table} * RB(t) \quad \text{Equation (2)}$$

As is obvious from the equations (1) and (2), a difference between the elution responses RA(t) and RB(t) of the respective liquid chromatographs A and B becomes a difference in the measurement results in a case where the same time table (Time Table) is input to the respective liquid chromatographs A and B.

Next, in the system conversion processing device 107, the trans (Trans(t)) between the elution responses RA(t) and RB(t) of the liquid chromatographs A and B is acquired by the trans calculator 403 (S304).

[MATH. 3]

$$RA(t)=RB(t)*\mathrm{Trans}(t)=\int_{-\infty}^{\infty}RB(t')\cdot\mathrm{Trans}(t-t')dt' \quad \text{Equation (3)}$$

Here, the trans (Trans(t)) between the elution responses of the liquid chromatographs A and B is calculated by deconvolution calculation of the above-described equation (3). A time table (Time Table B(t)) made in order to obtain the same measurement results as those of the liquid chromatograph A in the liquid chromatograph B is calculated by the following equation (4) using the original time table (Time Table A(t)) and the Trans(t). For this reason, the conversion time table calculator 404 of the system conversion processing device 107 calculates the time table (Time Table B(t)) made in consideration of the trans between the elution responses RA(t) and RB(t) of the liquid chromatographs A and B based on the equation (4) while reading the time table (Time Table A(t)) which is a target to be converted from the time table storage unit 406 (S305).

[MATH. 4]

$$\text{Time Table } B(t)=\text{Time Table } A(t)*\mathrm{Trans}(t)= \\ \int_{-\infty}^{\infty}\text{Time Table } A(t')\cdot\mathrm{Trans}(t-t')dt' \quad \text{Equation (4)}$$

The conversion time table calculator 404 outputs the time table (converted time table: Time Table B(t)) calculated in S305 to the time table storage unit 406 of the data processing device 106 (S306). The pump control unit 407 of the data processing device 106 controls the pumps 102A and 102B based on the time table (Time Table B(t)) (S307). In this manner, since the time table (Time Table B(t)) necessary for obtaining the same measurement results as those of the liquid chromatograph A in the liquid chromatograph B can be shown by the convolution of the trans (Trans(t)) between the elution responses of the liquid chromatographs A and B and the existing time table (Time Table A(t)), the same measurement results as those of the liquid chromatograph A can be obtained in the liquid chromatograph B using the existing time table (Time Table A(t)) when the trans (Trans (t)) between the elution responses is calculated.

Further, in the present example, as the hardware configuration at the time of acquiring the elution response, a hardware configuration in which the detector 105 is directly connected to an outlet of the auto sampler 103 to which the analysis column 207 is generally connected can be exemplified. The elution response can be acquired by measuring the absorbance of the eluent sent from the pump 102A and the pump 102B using the detector 105. By employing such a configuration, the elution response caused by the pumps and the auto sampler can be obtained. In addition, the detector 105 may be normally connected to the outlet of the auto sampler 103 through the analysis column 207. In the latter case, a resistance tube in place of the analysis column 207 is connected to the outlet of the auto sampler 103, the detector 105 is connected to the resistance tube, and the elution response may be acquired. Moreover, from a viewpoint of acquiring the elution response, it is preferable that the resistance pipe and the column have a low capacity since the influence of the resistance tube or the column is suppressed. In addition, the case where the sample injection unit is the auto sampler 103 has been described here, but the sample injection unit may be a manual injector.

Figure 5:
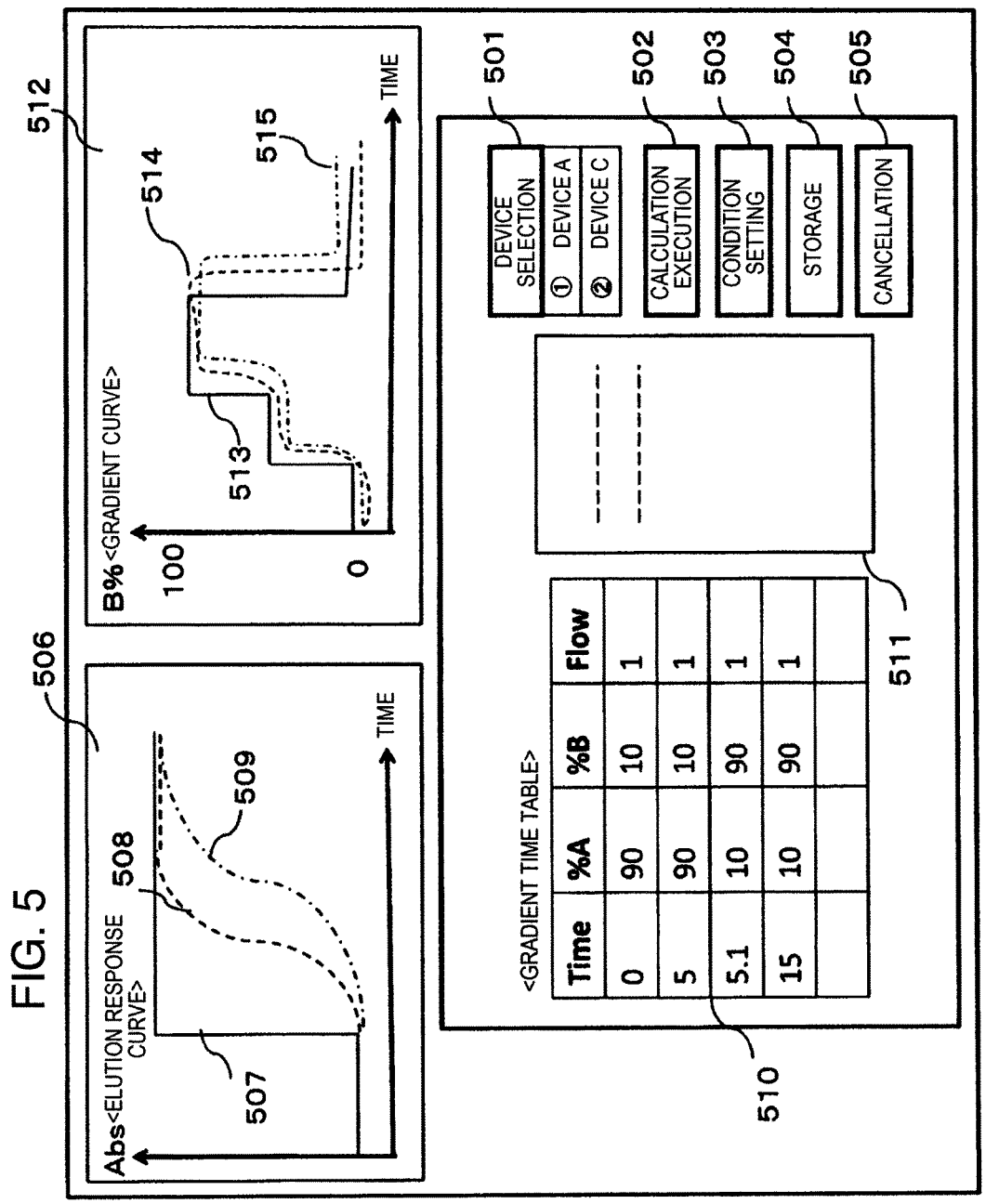
FIG. 5 is a view illustrating an example of a display screen of an output device 109 of the present invention.

FIG. 5 illustrates a display screen of the output device 109 at the time of setting the system conversion according to the present embodiment.

An elution response curve display unit 506, a gradient table display unit 510, a gradient curve display unit 512, a device selection button 501, a calculation execute button 502, a condition setting button 503, a storage button 504, a cancel button 505, a message display unit 511 are provided on the display screen illustrated in the figure.

The elution response curve display unit 506 is a portion on which a command value 507 used for measuring an elution response, an elution response 508 by itself (liquid chromatograph B), and an elution response 509 of another device (liquid chromatograph A) which reproduces measurement results are displayed. In the illustrated example, it is understood that the command value 507 is stepwise and the liquid chromatograph B (elution response 508) responds more rapidly compared to the liquid chromatograph A (elution response 509). Specific examples of the command value 507 will be described below.

The gradient time table display unit 510 is a portion on which a time table (time table before being converted) used for sample measurement is displayed. In the illustrated example, a time table which is the same as that illustrated in FIG. 7 is used and displayed. The time table being used for measurement may be newly set by being input to a table on the display screen of the output device 109 through the input device 108 or the existing time table may be read from the time table storage unit 406.

The gradient curve display unit 512 is a portion on which a graph shape 513 of a time table displayed on the gradient table display unit 510; an actual elution profile (actual gradient curve) 514 when the liquid chromatograph B is controlled by itself (liquid chromatograph B) based on the time table; and an actual elution profile (actual gradient curve) 515 at the time when measurement results of another device (liquid chromatograph A) are reproduced by itself based on the trans between the time table and the elution profile are displayed.

The device selection button 501 is a button for selecting another device at the time when measurement results are reproduced. As a specific method of selecting a device, for example, when the device selection button 501 is pressed by the input device 108 such as a pointing device or the like, a plurality of device names in which elution responses are stored in the elution response storage unit 402 are displayed on a screen and one of the devices is selected by the operator through the input device 108.

The calculation execute button 502 is a button for executing a process (S304) of acquiring a trans between elution responses of the device (liquid chromatograph A) selected through the device selection button 501 and itself (liquid chromatograph B) and a process (S305) of acquiring a time table made in consideration of the trans using the system conversion processing device 107.

The condition setting button 503 is a button for outputting a time table (converted time table) calculated by pressing the calculation execute button 502 to the data processing device 106 (S306) and setting the time table to be used for control of the pumps 102.

Here, when the storage button 504 is clicked, the results of the system conversion under the above-described conditions can be stored in the storage unit (not illustrated) of the data processing device.

Further, when the cancel button 505 is clicked, the arithmetic processing in the past is cancelled and the state can be returned to the state before the system conversion process is performed.

The message display unit 511 is a portion on which messages or the like related to the operation and the process of the liquid chromatograph are displayed.

Figure 6:
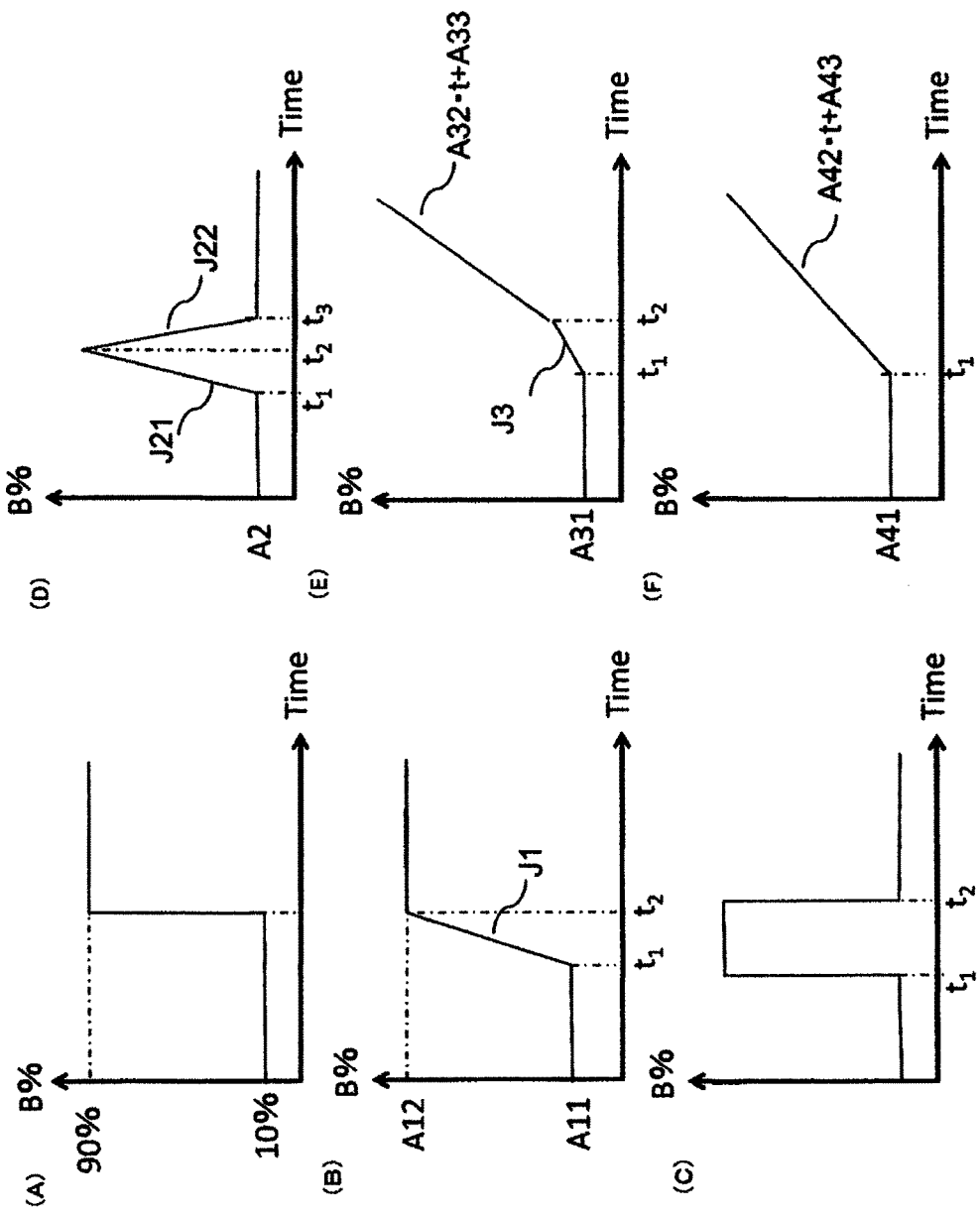
FIG. 6 is a diagram illustrating an example of a time table (command value) to be input in order to acquire an elution response of the liquid chromatograph according to the present invention.

FIG. 6 illustrates an example of the elution time table (command value) to be input in order to acquire elution responses of the respective liquid chromatographs. The command value regulates the control of the pumps 102 at the micro time of an order of several milliseconds to several seconds. In FIGS. 6(A) to 6(F), the timing at which the mixing ratio of an eluent is switched in each mobile phase varies. In addition, "B %" in FIG. 6 indicates a composition ratio of the eluent 201B in the mobile phase. Hereinafter, specific examples of the command value to be input to the pumps 102 at the time when the elution response is acquired will be described below with reference to the figure.

First, as an example of the command value, a command value that changes the mixing ratio of two types of eluents while the total flow rate of two types of the eluents (eluents 201A and 201B) is maintained to be constant as the step function illustrated in FIG. 6(A) can be exemplified. As the method of calculating the elution response in this case, a method of calculating the elution response by normalizing a difference between an observation value at the time when the observation value before an eluent is switched on a gradient curve to be measured enters a static state and an observation value at the time when the observation value after the eluent is switched on the gradient curve enters a static state is set as 1 and calculating a differential or a delta of the gradient curve can be exemplified.

In addition, as an example of the command value, a command value that switches an eluent as in the example of FIG. 6(B), that is, H1(t) of the following equation (5) can be exemplified. In addition, a difference between an observation value at the time when the observation value before an eluent is switched on a gradient curve enters a static state and an observation value at the time when the observation value after the eluent is switched on the gradient curve enters a static state is normalized as 1. The elution response is acquired by calculating a differential or a delta of the gradient curve.

[MATH. 5]

$$H1(t) = \begin{cases} A12 & (t \geq t_2) \\ J1(t) & (t_2 \geq t \geq t_1) \\ A11 & (t_1 \geq t) \end{cases} \quad \text{Equation (5)}$$

Here, A11 and A12 represent a constant and A12 is set to be larger than A11. $t_1$ and $t_2$ are not in a relationship of "$t_1=t_2$." It is preferable that a difference between $t_2$ and $t_1$ is in the range of milliseconds to seconds.

Further, H1(t) is continuous in a case of "t=$t_1$, $t_2$" as a boundary condition. That is, a relationship of "J1($t_1$)=A11" is satisfied in a case of "t=$t_1$," and a relationship of "J1($t_2$)=A12" is satisfied in a case of "t=$t_2$."

J1(t) is a monotonically increasing function and examples of J1(t) include a polynomial, an exponential function, and a function combining these.

Moreover, as an example of the command value, a command value of switching an eluent as in a case of a boxcar function illustrated in FIG. 6(C) can be exemplified. The area of a peak after the gradient curve is measured is calculated and the gradient curve is normalized such that the area of the peak becomes 1.

Moreover, as an example of the command value, a command value of switching an eluent as in a case illustrated in FIG. 6(D), that is, H2(t) of the following equation (6) can be exemplified.

[MATH. 6]

$$H2(t) = \begin{cases} A2 & (t \geq t_3) \\ J22(t) & (t_3 \geq t \geq t_2) \\ J21(t) & (t_2 \geq t \geq t_1) \\ A2 & (t_1 \geq t) \end{cases} \quad \text{Equation (6)}$$

Here, A2 represents a constant. Further, in regard to $t_1$, $t_2$, and $t_3$, relationships of "$t_1=t_2$" and "$t_2=t_3$" are not satisfied. It is preferable that a difference between $t_1$ and $t_2$ and a difference between $t_2$ and $t_3$ are in the range of milliseconds to seconds.

H2(t) of the equation (6) is continuous in a case of "t=$t_1$, $t_2$, $t_3$" as a boundary condition. That is, a relationship of "J21($t_1$)=A2" is satisfied in a case of "t=$t_1$," a relationship of "J21($t_2$)=J22($t_2$)" is satisfied in a case of "t=$t_2$," and a relationship of "J22($t_3$)=A2" is satisfied in a case of "t=$t_3$." J21(t) of Math. 5 is a monotonically increasing function and examples of J21(t) include a monotonically increasing polynomial, a monotonically increasing exponential function, and a function combining these. J22(t) of the equation (6) is a monotonically decreasing function and examples of J22(t) include a monotonically decreasing polynomial, a monotonically decreasing exponential function, and a function combining these.

As another example of the command value, a command value of switching an eluent as in a case of FIG. 6(E), that is, H3(t) of the following equation (7) can be exemplified. The eluent is switched on the gradient curve, a second order differential of the gradient curve is calculated, and the area of the peak is normalized as 1.

[MATH. 7]

$$H3(t) = \begin{cases} A32 \cdot t + A33 & (t \geq t_2) \\ J3(t) & (t_2 \geq t \geq t_1) \\ A31 & (t_1 \geq t) \end{cases} \quad \text{Equation (7)}$$

Here, A31, A32, and A33 of the equation (7) represent a constant. In addition, $t_1$ and $t_2$ of the equation (7) are not in a relationship of "$t_1=t_2$." It is preferable that a difference between $t_2$ and $t_1$ is in the range of milliseconds to seconds.

H3(t) of the equation (7) is continuous in a case of "t=$t_1$, $t_2$" as a boundary condition. That is, a relationship of "J3($t_1$)=A31" is satisfied in a case of "t=$t_1$" and a relationship of "J3($t_2$)=A32·$t_2$+A33" is satisfied in a case of "t=$t_2$." J3(t) of the equation (7) is a monotonically increasing function. Examples of J3(t) of the equation (7) may include a polynomial, an exponential function, and a function combining these.

Further, as an example of the command value, a command value of switching an eluent as in a case of FIG. 6(F), that is, H4(t) of the following equation (8) can be exemplified. The elution response can be acquired by inputting the time table and measuring the gradient curve. For example, the eluent is switched on the gradient curve, a second order differential of the gradient curve is calculated, and the area of the peak is normalized as 1.

[MATH. 8]

$$H4(t) = \begin{cases} A42 \cdot t + A43 & (t \geq t_1) \\ A41 & (t_1 > t) \end{cases} \quad \text{Equation (8)}$$

Here, A41, A42, and A43 represent a constant and A42 is set to be larger than A41.

H4(t) of the equation (8) is continuous in a case of "$t=t_1$" as a boundary condition. That is, a relationship of "$H4(t_1)=A42 \cdot t_1 + A43$" is satisfied in a case of "$t=t_1$."

As illustrated above, a plurality of methods of determining elution responses are present. In Math. 1, it is preferable that the method of determining the elution response of the liquid chromatograph A is the same as the method of determining the elution response of the liquid chromatograph B, but the determining methods may be different from each other.

In this manner, an elution response of a liquid chromatograph can be acquired corresponding to elution responses of various gradients.

Example 2

Figure 8:
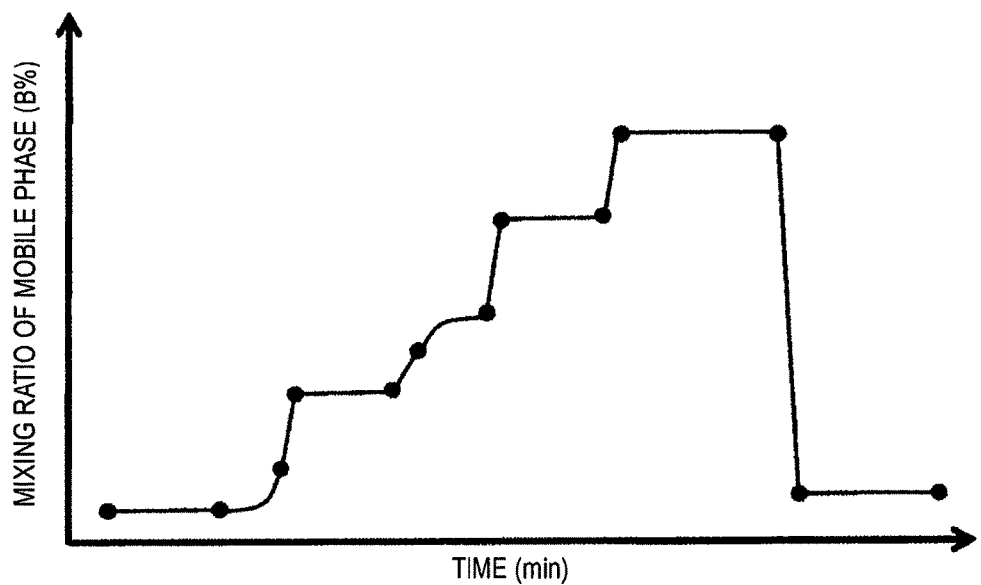
FIG. 8 is a graph illustrating an elution time table before system conversion.

FIG. 7 illustrates an elution time table before system conversion. In this case, in general, the total required time is divided into a plurality of intervals, the starting time and the ending time are set, a program for changing the composition ratio among respective eluents between the starting time and the ending time of respective intervals is designated, and data is transmitted to pumps. In addition, a graph illustrated in FIG. 8 is created by connecting data of acquired straight lines or elementary functions.

Figure 9:
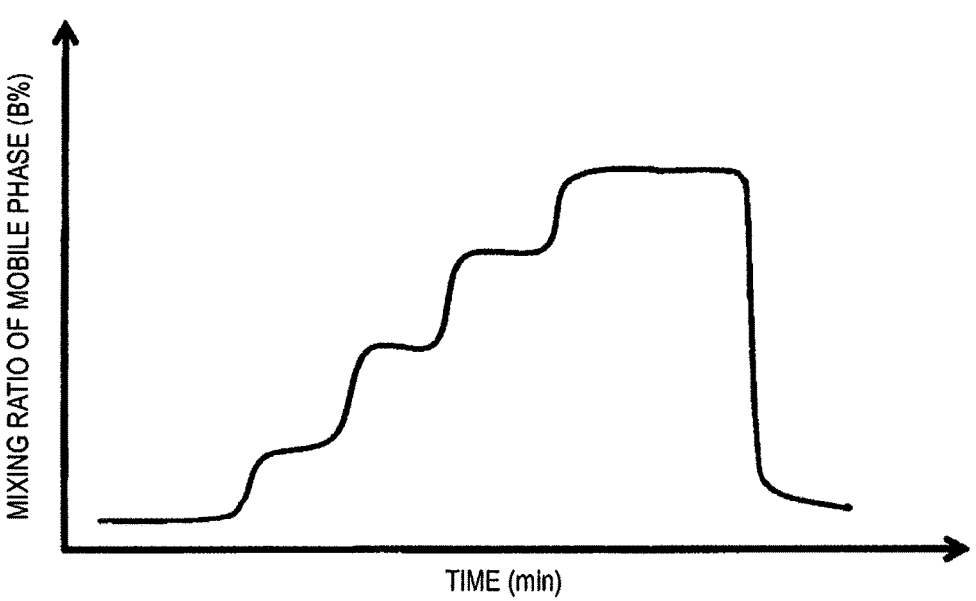
FIG. 9 is a graph illustrating an elution time table after system conversion.

Here, in a case where system conversion is performed using the above-described method, since a process is carried out such that one liquid chromatograph obtains the same measurement results as those of another liquid chromatograph, the elution time table made in consideration of the trans between the elution responses of both liquid chromatographs has a shape of a complicated curve which cannot be shown by straight lines or elementary functions illustrated in FIG. 9 and thus the amount of information becomes enormous. Accordingly, in a case where such data is transmitted to the pumps, this takes a long time and there is a possibility that the pumps cannot be accurately controlled while the data is transmitted. Further, a problem in that securing of the memory capacity has a cost is generated.

Here, in the present example, a data processing method when data is transmitted to the pumps 102 by performing the system conversion process described in Example 1 will be described.

Figure 10:
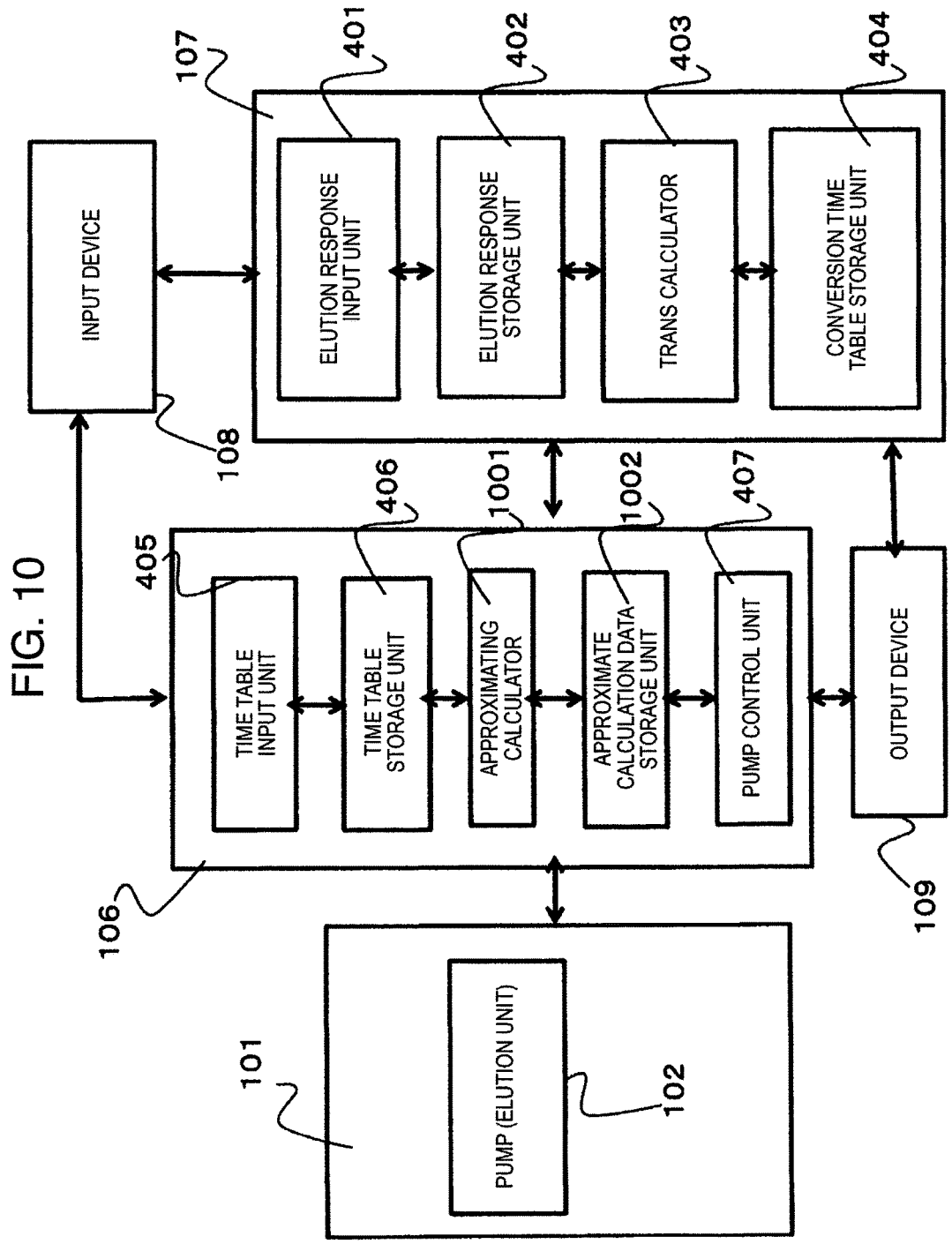
FIG. 10 is a diagram illustrating a part of a system configuration of a data processing device 106 and a system conversion processing device 107 according to Example 2 of the present invention.

FIG. 10 illustrates a part of a system configuration diagram of the data processing device 106 and the system conversion processing device 107 according to Example 2 of the present invention. The figure is different from the configuration diagram illustrated in FIG. 4 in that the data processing device 106 includes an approximating calculator 1001 and an approximate calculation data storage unit 1002.

The elution time table after system conversion between liquid chromatographs is calculated by the conversion time table calculator 404 in the system conversion processing device 107 in FIG. 10 and stored in the time table storage unit 406 of the data processing device 106.

An approximation curve related to a set approximating interval is calculated by the approximating calculator 1001 with respect to the elution time table stored in the time table storage unit 406 and the results are stored in the approximate calculation data storage unit 1002. In the approximate calculation data storage unit 1003, the stored approximating interval and data related to the created approximation curve are transmitted to the pump control unit 407.

Next, a specific calculation method in the approximating calculator 1001 will be described below.

Figure 11:
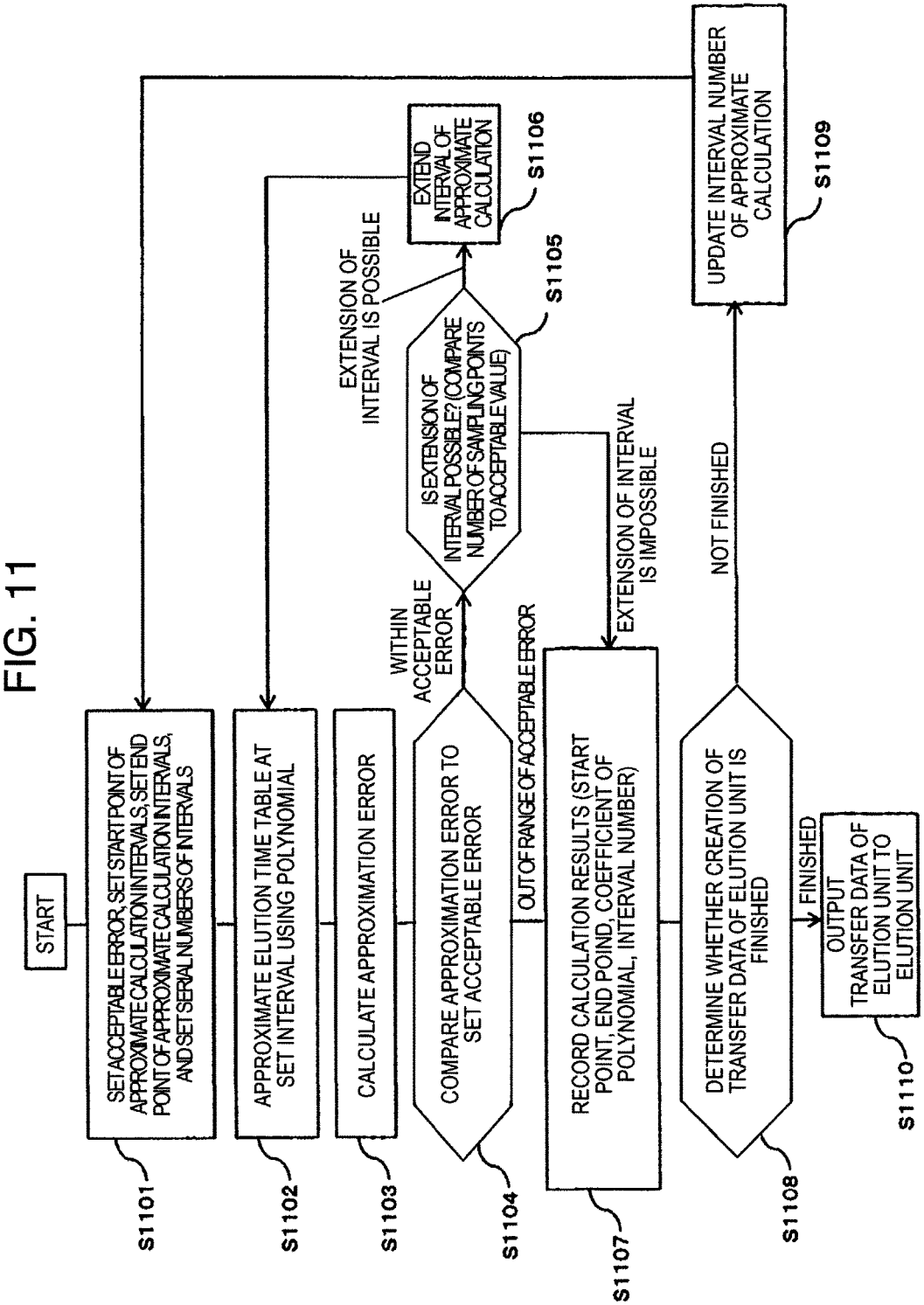
FIG. 11 is a flowchart illustrating a basic process of a process of approximate calculation according to the present invention.

FIG. 11 is a flowchart illustrating a basic process of the approximate calculation process of the present invention. In the present example, the elution time table is divided into a plurality of intervals such that the elution data amount and the calculation time are reduced within an acceptable error of approximation and is approximated using elementary functions or the like for each interval.

First, values of acceptable errors, start points and end points of intervals at which approximate calculation is performed, and serial numbers of the intervals are set (S1101). At this time, an interval to be set has a minimum range in which desired approximate calculation is possible. For example, when third order polynomial approximation is performed, an interval is determined so as to include four points which is the minimum as the sampling interval.

Subsequently, the elution time table is obtained by approximate calculation using a polynomial within the set interval (S1102) and the approximation error is acquired (S1103). The acquired approximation error is compared to the value of the acceptable error set in advance in S1101 (S1104) and the calculation results are recorded in a case where the acquired approximation error exceeds the acceptable error (S1107). Here, start points, end points, coefficients of polynomials, interval numbers, and the like are recorded.

At this time, the first result is recorded when the approximate calculation is carried out for the first time and the previous result (previous result of the calculation) is recorded when the approximate calculation is carried out for the second or subsequent time (S1107).

After the results are recorded, completion determination of transfer data of an elution unit is performed based on whether the calculated interval is final (S1108). In a case where the calculated interval is final, the calculation result is output to the elution unit and the process ends (S1110). Meanwhile, in a case where the calculated interval is not final, the calculation result is updated to the interval number in which subsequent approximate calculation is performed (S1109) and the process is returned to S1101 again.

Moreover, when the approximation error does not exceed the acceptable error, it is determined whether extension of the interval is carried out (S1105). Here, it is determined that the approximating interval is set to be as long as possible in order to reduce the amount of information to be sent to the elution unit. However, since it takes time to acquire the approximation curve when the interval becomes extremely long, the length of the interval, that is, the upper limit of the number of sampling points from the start point to the end point is determined and it is determined whether extension of the interval is possible based on the upper limit.

In a case where extension of the interval is possible, the number of sampling points is increased (S1106). At this time, it is preferable to increase the sampling points one by one in order to improve the precision. Further, the above-described approximate calculation is performed again in a newly set interval (S1102).

Figure 12:
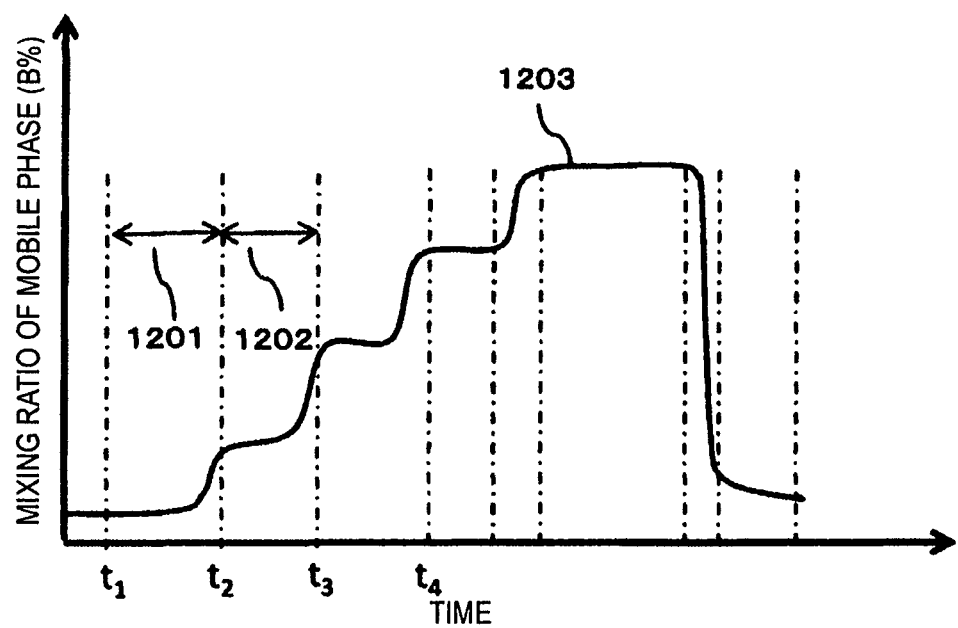
FIG. 12 is a graph illustrating an example of an elution time table after the process of approximate calculation according to the present invention.

FIG. 12 is a graph illustrating the elution time table after the approximate calculation. As illustrated in the figure, the elution time table after the system conversion process is performed is divided into the most suitable approximating intervals.

Here, as described above, when the interval approximated in the approximate calculation becomes longer, it takes a long time for carrying out the calculation process. The time for the approximate calculation is exponentially increased with respect to the number of pieces of data. The relationship between a time T and the number n of pieces of data of the approximate calculation is shown by the equation (8). At this time, the value acquired by the equation 9 can be used as an upper limit J of the length of the approximating interval.

[MATH. 9]

$$T = A \times \exp(B \times n) \quad \text{Equation (9)}$$

[MATH. 10]

$$J = 1/B \quad \text{Equation (10)}$$

Upper Limit of Length of Approximate Interval

In the present example, as a method of approximation of the elution time table at the set approximating interval using elementary functions, a method of approximation using a polynomial as described above can be performed. In this case, a pseudo inverse matrix of Moore-Penrose may be used in the approximate calculation.

In the present example, the approximation curve is compared to the elution time table, an absolute value of a difference between an elution time table Yi and an approximate value yj thereof in the equation (9) is calculated in the entire range of the approximating interval, and then the absolute value can be set as the maximum value thereof as a method of calculating the approximation error.

[MATH. 11]

$$\text{Max}(|Yi - yj|) \quad \text{Equation (11)}$$

In the present embodiment, data stored in an approximation curve result storage unit is described with reference to a case where a third order polynomial shown in the equation (11) is set as an approximation curve. FIG. 13 is a diagram showing a table of approximate calculation results. As illustrated in the figure, for example, serial numbers at respective approximating intervals, the starting time at respective approximating intervals, the ending time at respective approximating intervals, a coefficient $a_0$ of a constant term of a polynomial, a coefficient $a_1$ of t, a coefficient $a_2$ of $t^2$, and a coefficient $a_3$ of $t^3$ at respective approximating intervals are recorded.

[MATH. 12]

$$a_0 + a_1 t + a_2 t^2 + a_3 t^3 \quad \text{Equation (12)}$$

REFERENCE SIGNS LIST

101: Liquid chromatograph unit
102: Pump
103: Auto sampler
104: Column oven
105: Detector
106: Data processing device
107: System conversion processing device
108: Input device
109: Output device
110: Control unit
201A, 201B: Eluent
203: Mixer
205: Washing solution
207: Analysis column
401: Elution response input unit
402: Elution response storage unit
403: Trans calculator
404: Conversion time table calculator
405: Time table input unit
406: Time table storage unit
407: Pump control unit
501: Device selection button
502: Calculation execute button
503: Condition setting button
504: Storing button
505: Cancel button
506: Elution response curve display unit
507: Command value
508: Elution response of liquid chromatograph B
509: Elution response of liquid chromatograph A
510: Gradient time table display unit
511: Message display unit
512: Gradient curve display unit
513: Graph shape of time table
514: Gradient curve of liquid chromatograph B
515: Gradient curve of liquid chromatograph A
1001: Approximating calculator
1002: Approximate calculation data storage unit
1201, 1202: Approximating interval
1203: Elution time table after system conversion

The invention claimed is:

1. A first liquid chromatograph comprising:
a first liquid chromatograph unit which includes a first elution unit which pumps an eluent;
a first detecting unit which measures a component of a sample injected with the eluent pumped from the first elution unit; and
a control unit which controls elution performed by the first elution unit,
wherein the control unit includes:
an elution response storage unit which stores a first elution response of the first liquid chromatograph unit obtained by detection when a plurality of command values of a first time table are input to the first elution unit and stores a second elution response of a second liquid chromatograph, different from the first liquid chromatograph, obtained by detection when the plurality of command values of the first time table are input to a second elution unit of the second liquid chromatograph,
a conversion time table calculator which converts the first time table into a second time table based on the first elution response and the second elution response such that a first elution profile at a time when the first elution unit is controlled by the first liquid chromatograph unit based on the first time table approaches a second elution profile at a time when the second elution unit is controlled by the second liquid chromatograph based on the first time table, and
an approximating calculator which divides the second time table into a plurality of regions, performs a plurality of approximate calculations for each of the divided regions of the second time table, and changes the plurality of regions of the second time table based on a result of the approximate calculations,
wherein the control unit controls elution of the eluent pumped by the first elution unit based on the second time table divided into the plurality of regions.

2. The liquid chromatograph according to claim 1, wherein the approximating calculator performs a plurality of polynomial approximations as the approximate calculations and obtains an approximation error of the approximate calculations for the second time table.

3. The liquid chromatograph according to claim 1,
wherein the approximating calculator changes the regions into which the second time table is divided based on whether an approximation error of the approximate calculations exceeds a predetermined threshold value.

4. The liquid chromatograph according to claim 1,
wherein the approximating calculator changes the regions into which the second time table is divided to be larger in size in a case where an approximation error of the approximate calculations does not exceed a predetermined threshold value.

5. The liquid chromatograph according to claim 4,
wherein the approximating calculator sets an upper limit in advance of a size of the regions to be divided for the second time table.

6. The liquid chromatograph according to claim 1,
wherein the first elution profile is a first gradient curve and the second elution profile is a second gradient curve.

7. The liquid chromatograph according to claim 1,
wherein performing the plurality of approximate calculations for each of the divided regions of the second time table generates an approximation curve for the second time table.

8. A method of processing data of a liquid chromatograph, the method comprising:
acquiring a first elution response regarding a first liquid chromatograph by detection when a plurality of command values of a first time table are input to a first elution unit of the first liquid chromatograph;
acquiring a second elution response regarding a second liquid chromatograph by detection, different from the first liquid chromatograph, when the plurality of command values of the first time table are input to a second elution unit of the second liquid chromatograph;
converting the first time table into a second time table based on the first elution response and the second elution response such that a first elution profile at a time when the first elution unit is controlled by the first liquid chromatograph unit based on the first time table approaches a second elution profile at a time when the second elution unit is controlled by the second liquid chromatograph based on the first time table;
dividing the second time table into a plurality of regions;
performing a plurality of approximate calculations for each of the divided regions of the second time table, and changing the plurality of regions of the second time table based on a result of the approximate calculations; and
controlling elution of an eluent pumped by the first elution unit of the first liquid chromatograph based on the second time table divided into the plurality of regions.

9. The method according to claim 8,
wherein the first elution profile is a first gradient curve and the second elution profile is a second gradient curve.

10. The method according to claim 8,
wherein performing the plurality of approximate calculations for each of the divided regions of the second time table generates an approximation curve for the second time table.

11. The method according to claim 8,
wherein performing the plurality of approximate calculations for each of the divided regions of the second time table comprises performing a plurality of polynomial approximations as the approximate calculations and obtaining an approximation error of the approximate calculations for the second time table.

12. The method according to claim 8, further comprising:
changing the regions into which the second time table is divided based on whether an approximation error of the approximate calculations exceeds a predetermined threshold value.

13. The method according to claim 8, further comprising:
changing the regions into which the second time table is divided to be larger in size in a case where an approximation error of the approximate calculations does not exceed a predetermined threshold value.

14. The method according to claim 13, further comprising:
setting an upper limit in advance of a size of the regions to be divided for the second time table.

15. A liquid chromatograph apparatus comprising:
a first liquid chromatograph unit which includes a first elution unit which pumps an eluent;
a first detecting unit which measures a component of a sample injected with the eluent pumped from the first elution unit;
a second liquid chromatograph unit which includes a second elution unit which pumps an eluent;
a second detecting unit which measures a component of a sample injected with the eluent pumped from the second elution unit; and
a control unit which controls elution performed by the first elution unit,
wherein the control unit includes:
an elution response storage unit which stores a first elution response of the first liquid chromatograph unit obtained by detection when a plurality of command values of a first time table are input to the first elution unit and stores a second elution response of a second liquid chromatograph, different from the first liquid chromatograph, obtained by detection when the plurality of command values of the first time table are input to a second elution unit of the second liquid chromatograph,
a conversion time table calculator which converts the first time table into a second time table based on the first elution response and the second elution response such that a first elution profile at a time when the first elution unit is controlled by the first liquid chromatograph unit based on the first time table approaches a second elution profile at a time when the second elution unit is controlled by the second liquid chromatograph based on the first time table, and
an approximating calculator which divides the second time table into a plurality of regions, performs a plurality of approximate calculations for each of the divided regions of the second time table, and changes the plurality of regions of the second time table based on a result of the approximate calculations,
wherein the control unit controls elution of the eluent pumped by the first elution unit based on the second time table divided into the plurality of regions.

16. The liquid chromatograph apparatus according to claim 15,
wherein performing the plurality of approximate calculations for each of the divided regions of the second time table generates an approximation curve for the second time table.

17. The liquid chromatograph apparatus according to claim 15,
wherein the approximating calculator performs a plurality of polynomial approximations as the approximate calculations and obtains an approximation error of the approximate calculations for the second time table.

18. The liquid chromatograph apparatus according to claim 15,
wherein the approximating calculator changes the regions into which the second time table is divided based on whether an approximation error of the approximate calculations exceeds a predetermined threshold value.

19. The liquid chromatograph apparatus according to claim 15,
wherein the approximating calculator changes the regions into which the second time table is divided to be larger in size in a case where an approximation error of the approximate calculations does not exceed a predetermined threshold value.

20. The liquid chromatograph apparatus according to claim 19,
wherein the approximating calculator sets an upper limit in advance of a size of the regions to be divided for the second time table.

* * * * *